United States Patent
Akikaze et al.

(10) Patent No.: US 8,299,294 B2
(45) Date of Patent: Oct. 30, 2012

(54) PROCESS FOR PRODUCING VINYL SULFONIC ACID

(75) Inventors: Hiroshi Akikaze, Osaka (JP); Takehiko Miyai, Nobeoka (JP)

(73) Assignee: Asahi Kasei Finechem Co., Ltd., Osaka-Shi (JP)

( * ) Notice: Subject to any disclaimer, the term of this patent is extended or adjusted under 35 U.S.C. 154(b) by 69 days.

(21) Appl. No.: 12/448,607

(22) PCT Filed: Dec. 26, 2007

(86) PCT No.: PCT/JP2007/074933
§ 371 (c)(1),
(2), (4) Date: Jun. 26, 2009

(87) PCT Pub. No.: WO2008/078767
PCT Pub. Date: Jul. 3, 2008

(65) Prior Publication Data
US 2010/0081840 A1 Apr. 1, 2010

(30) Foreign Application Priority Data
Dec. 27, 2006 (JP) ................................. 2006-351663

(51) Int. Cl.
*C07C 309/21* (2006.01)
(52) U.S. Cl. ..................................................... 562/124
(58) Field of Classification Search .................. 564/124; 562/124
See application file for complete search history.

(56) References Cited

U.S. PATENT DOCUMENTS

| 2,597,696 A | | 5/1952 | Anthes et al. | |
| 2,619,452 A | | 11/1952 | Jones et al. | |
| 3,312,735 A | | 4/1967 | Medford et al. | |
| 6,156,207 A | * | 12/2000 | Hommeltoft et al. | ......... 210/681 |

FOREIGN PATENT DOCUMENTS
JP 2000-191629 7/2000

OTHER PUBLICATIONS

Sango Kunichika et al., Journal of the Chemical Society of Japan, Industrial chemistry section, vol. 64, No. 5, 1961, pp. 929-932 and the partial English translation thereof.
International Search Report dated Feb. 26, 2008, issued on PCT/JP2007/074933.
Supplementary European Search Report dated Nov. 14, 2011, issued for the corresponding European Patent Application No. 07 86 0162.2.
David S. Breslow et al., "The Synthesis and Polymerization of Ethylenesulfonic Acid," Journal of the American Chemical Society, vol. 76, No. 24, Dec. 20, 1954, pp. 6399-6401.

* cited by examiner

*Primary Examiner* — Peter G O Sullivan
(74) *Attorney, Agent, or Firm* — Edwards Wildman Palmer LLP; James E. Armstrong, IV; Nicholas J. DiCeglie, Jr.

(57) ABSTRACT

The subject invention provides:
a method for producing vinyl sulfonic acid, comprising conducting demetallation of vinyl sulfonate salt, wherein the demetallation rate is not less than 95% according to the following formula:

Demetallation rate(%)={(acid value after demetallation)/(acid value before demetallation)}×100;

a method for producing vinyl sulfonic acid, comprising conducting demetallation of vinyl sulfonate salt, wherein demetallation is carried out using a strongly acidic ion exchange resin; and
said method further comprising the step of purifying a product of the demetallation using a thin film evaporator.

2 Claims, No Drawings

PROCESS FOR PRODUCING VINYL SULFONIC ACID

FIELD OF THE INVENTION

The present invention relates to a method of producing vinyl sulfonic acid, particularly to a method of producing vinyl sulfonic acid, comprising a vinyl sulfonate salt demetallation process.

BACKGROUND ART

In recent years, vinyl sulfonic acid has attracted increasing attention as a monomer for use in composing performance polymers or conductive materials.

There are various methods for producing vinyl sulfonic acid (see Nonpatent-Document 1); however, existing methods are still not reliable enough for the industrial production of vinyl sulfonic acid.

For example, Patent-Document 1 discloses a method for producing vinyl sulfonic acid by removing sodium from sodium vinyl sulfonate using hydrochloric acid.

However, this method fails to ensure desirable product quality. Moreover, distillation of the vinyl sulfonic acid manufactured by this method produces a large amount of solid residue. For these reasons, this method is almost useless for industrial purposes.

Patent Document 2 discloses a method for producing vinyl sulfonic acid via dehydration of an isethionic acid using phosphorus pentoxide or pyrophosphoric acid as a dehydration agent. However, this method uses a large amount of dehydration agent, and requires disposal of the dehydration agent. For this reason, this method is not suitable for industrial purposes.
Patent-Document 1: U.S. Pat. No. 3,312,735
Patent Document 2: U.S. Pat. No. 2,597,696
Nonpatent-Document 1: Sango Kunichika, Takao Katagiri, Journal of the Chemical Society of Japan, Industrial chemistry section, Vol. 64 No. 5, 1961, pp. 929-932

DISCLOSURE OF THE INVENTION

Problem to be Solved by the Invention

An object of the present invention is to provide an industrial method for producing vinyl sulfonic acid.

Means for Solving the Problem

In order to solve the foregoing problems, the inventors of the present invention conducted intensive study and found a method ensuring an improved yield. The method uses vinyl sulfonate, and carries out a demetallation process with an ion exchange resin at a metal-hydrogen exchange rate equal to or greater than a predetermined value. With further research on this method, the inventors eventually completed the present invention.

That is, the present invention relates to the following production methods.

Item 1: A method of producing vinyl sulfonic acid, comprising the step of conducting demetallation of vinyl sulfonate salt, wherein a demetallation rate is not less than 95% according to the following formula:

Demetallation rate(%)={(acid value after demetallation)/(acid value before demetallation)}×100.

More preferably, the method according to Item 1, wherein the vinyl sulfonate salt is sodium vinyl sulfonate, and the metal is sodium.

Item 2: A method of producing vinyl sulfonic acid, comprising the step of conducting demetallation of vinyl sulfonate salt, wherein the demetallation is carried out using a strongly acidic ion exchange resin.

More preferably, the method according to Item 2, wherein a demetallation rate is not less than 95% according to the following formula:

Demetallation rate(%)={(acid value after demetallation)/(acid value before demetallation)}×100.

More preferably, the method according to Item 2, wherein the vinyl sulfonate salt is sodium vinyl sulfonate, and the metal is sodium.

Item 3: The method according to Item 1 or 2, further comprising the step of purifying a product of the demetallation by thin film distillation.

More preferably, the method according to Item 1 or 2 comprising the steps of conducting demetallation of vinyl sulfonate salt, wherein the demetallation rate is not less than 95% according to the following formula:

Demetallation rate(%)={(acid value after demetallation)/(acid value before demetallation)}×100;

and
purifying the product of the demetallation using a thin film evaporator.

More preferably, the method according to Item 1 or 2 comprising the steps of conducting demetallation by contacting a strongly acidic ion exchange resin with vinyl sulfonate salt; and purifying the product of the demetallation by thin film distillation.

The following more specifically describes the present invention.

1. Vinyl Sulfonate Salt

The present invention produces vinyl sulfonic acid using vinyl sulfonate salt.

Examples of vinyl sulfonate salt include the sodium salt, potassium salt, lithium salt, and mixtures of these. Among these, sodium vinyl sulfonate is particularly suitable.

The vinyl sulfonate salt may be a composition. For example, it is possible to use a composition made up of vinyl sulfonate salt, an isethionic acid salt, a salt of bis sulfoethyl ether, and the like.

When using such a composition, the percentage of vinyl sulfonate salt in the whole composition is usually not less than approximately 25%.

2. Demetallation

In this specification, "demetallation" designates a process for removing metal from vinyl sulfonate salt and exchanging it for hydrogen. In other words, demetallation designates a process for removing metal ions from vinyl sulfonate salt so as to convert the vinyl sulfonate salt into vinyl sulfonic acid.

The demetallation process can be expressed by the following general formula.

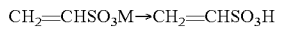

(Here, M represents a metal that forms a salt, i.e., sodium, potassium, etc.)

(1) Demetallation Rate

In the present invention, the demetallation rate is preferably not less than 95%, more preferably not less than 97%, and still more preferably not less than 99%.

In this specification, the demetallation rate designates a value denoted by the following formula.

Demetallation rate(%)={(acid value after demetallation)/(acid value before demetallation)}×100

The demetallation rate can be described as the rate of metal for hydrogen exchange in a material, for example, the rate of sodium for hydrogen exchange (sodium exchange rate). The demetallation rate can be otherwise described as the reduction rate of a metal salt compound contained in a material.

The demetallation rate can be found by measuring the acid value using a publicly known method. For example, the demetallation rate can be found by measuring the acid value by means of neutralization titration.

If the demetallation rate is 95% or greater, decomposition of the compound or the influence thereof is significantly reduced. Further, it becomes possible to adopt thin film distillation for the purification process after demetallation. Given this, large volume distillation can be performed at a high recovery rate.

Also, since it becomes possible to obtain high-quality vinyl sulfonic acid, the vinyl sulfonic acid after distillation is less colored. Furthermore, this vinyl sulfonic acid causes less coloration with time.

Any method in which the demetallation rate is not less than 95% can be adopted. A method using a strongly acidic ion exchange resin is however particularly preferable.

(2) Method Using a Strongly Acidic Ion Exchange Resin

In the present invention, it is preferable to perform demetallation using a strongly acidic ion exchange resin.

In other words, it is preferable to perform demetallation by contacting a strongly acidic ion exchange resin with vinyl sulfonate salt.

Any common method can be used to contact a strongly acidic ion exchange resin with vinyl sulfonate salt. However, to secure ion exchange, a method of filling a column with an ion exchange resin and making a vinyl sulfonate salt aqueous solution flow through the column is preferred.

Insofar as the effects of the present invention are not impaired, any useful resin can be selected from publicly known strongly acidic ion exchange resins. One example may be an insoluble cross-linked organic polymer compound containing a strong acid group on a side chain. Examples of such a strong acid group include sulfate groups, phosphate groups, sulfonic groups, and the like.

More specifically, Diaion® (SK1B, SK116, PK216 etc.), Amberlite® (IR-120B, IR-124 etc.), Dowex® (50wx8, HCR-S, Monosphere 650C etc.), or Lewatit® (S-100 etc.) can be used.

By performing demetallation using a strongly acidic ion exchange resin, vinyl sulfonate salt can be reduced at a high rate. Further, decomposition of the compound is suppressed, and the yield increases.

Moreover, the obtained vinyl sulfonic acid is of a high quality and causes less coloration.

With the usage of a strongly acidic ion exchange resin, demetallation can be efficiently performed via a single step process.

It also becomes possible to adopt thin film distillation in the subsequent purification process, which makes large volume distillation possible.

In demetallation using a strongly acidic ion exchange resin, the demetallation rate is preferably not less than 95%, more preferably not less than 97%, further preferably not less than 99%, so as to reduce gas generation and to increase the distillation recovery rate.

3. Thin Film Distillation Process

It is preferable to further purify the product of the above-mentioned demetallation, using a publicly known method.

The product of demetallation here designates a product resulting from demetallation of vinyl sulfonate salt or a composition thereof; more specifically, a vinyl sulfonic acid or a composition thereof obtained by demetallation.

An appropriate purification method can be selected from various publicly known methods; however, purification by distillation, particularly by thin film distillation, is preferred.

By adopting thin film distillation to purify the product, it becomes possible to obtain a high-quality vinyl sulfonic acid that is less colored at the time of distillation, and causes less coloration with time. Further, it becomes possible to purify a large quantity at a high recovery rate.

Thin film distillation can be performed in accordance with any publicly known method.

The conditions of the thin film distillation can be set according to the circumstances. The temperature range is usually from approximately 150 to approximately 250° C., preferably from approximately 150 to approximately 200° C. The pressure range is usually from approximately 30 to approximately 400 Pa, preferably from approximately 30 to approximately 200 Pa. Such conditions ensure better control of decomposition and polymerization.

The thin film distillation may be conducted twice or more as needed. Continuous distillation is also possible.

Any publicly known evaporators can be used for the thin film distillation apparatus. An evaporator having a tantalum portion as the part to be in contact with the fluid containing vinyl sulfonic acid is, however, preferable in view of reduced corrosion.

It is preferable to conduct thin film distillation with respect to a product resulting from demetallation of vinyl sulfonate salt in which the demetallation rate is set to 95% or greater.

It is also preferable to conduct thin film distillation on a product resulting from demetallation of vinyl sulfonate salt using a strongly acidic ion exchange resin. It is particularly preferable to conduct thin film distillation on a product resulting from demetallation of vinyl sulfonate salt when the demetallation is carried out at a demetallation rate of 95% or greater by contacting a strongly acidic ion exchange resin with vinyl sulfonate salt.

With such a product, decomposition of the compound due to distillation rarely occurs during thin film distillation, and the recovery rate increases. Further, gas generation is reduced during distillation, and the decompression degree becomes stable.

Also, continuous distillation and large volume distillation become possible.

Moreover, the resulting residue is not a high-viscosity solid, but a fluid. This eases cleaning of the device or facility.

Furthermore, the resulting vinyl sulfonic acid is of a high quality. Particularly, the vinyl sulfonic acid resulting from such distillation is almost colorless. It is also possible to obtain vinyl sulfonic acid that causes less coloration with time.

4. Other Processes

The production method of the present invention may further comprise additional steps other than the above-mentioned demetallation step and distillation step, as needed. For example, a raw-material purification step can be added.

Further, any known art or arts regarding the production of vinyl sulfonic acid can be combined with the method of the present invention, as needed.

5. Characteristics

The vinyl sulfonic acid obtained using the method of the present invention is of a high quality, is less colored, and causes less coloration with time.

With such outstanding characteristics, the vinyl sulfonic acid obtained by the method of the present invention can be suitably used as a material for an electrolyte membrane or an aqueous solution agent for a coating composition, a binder, etc., for example.

EFFECT OF THE INVENTION

The present invention provides efficient mass production of high-quality vinyl sulfonic acid, thereby significantly increasing vinyl-sulfonic-acid productivity.

Although various synthesizing methods are known as production methods for vinyl sulfonic acid, they have problems relating to complicated processes, low yields, and limit the scale of distillation. Therefore, they are almost useless for industrial purposes.

In contrast, the production method of the present invention suppresses compound decomposition, thereby significantly increasing the yield. Also, as it requires only a single step process, production can be performed in a simple manner.

Moreover, gas generation is reduced during distillation and the decompression degree becomes stable, the recovery rate increases. Further, the process produces only fluid residues that can be easily washed away from the device or the facility.

Further, since the method allows adoption of thin film distillation, the process scale can be increased. As a result, productivity significantly increases.

The method of the present invention provides high-quality vinyl sulfonic acid. This method suppresses the problems of coloration and coloration with time.

The present invention provides a superior method and means for use in the industrial production of vinyl sulfonic acid, thereby making practical industrial production of vinyl sulfonic acid possible.

BEST MODE FOR CARRYING OUT THE INVENTION

The following more specifically explains the present invention with examples and comparative examples. The present invention is, however, not limited to these examples.
Material and Measuring Method Sodium vinyl sulfonate was used as the vinyl sulfonate salt in the following embodiments.

The acid value and iodine value were measured according to Japanese Industrial Standard: JIS K0070-1992. The acid value was measured using neutralization titration.

According to the measured value of the acid value, the demetallation rate (sodium removal rate) was determined using the following formula.

Demetallation rate(%)={(acid value after demetallation)/(acid value before demetallation)}×100

According to the measured iodine value, the production yield was found using the following formula.

Yield(%)={(iodine value after demetallation)/(iodine value before demetallation)}×100

According to the measured iodine value, the recovery rate of the distillation process was found using the following formula.

Recovery rate(%)={(iodine value after distillation)/(iodine value before distillation)}×100

Unless otherwise specified, "%" in each example represents mol % and "Yield" represents mol yield.

COMPARATIVE EXAMPLE 1

Sodium Removal Process Using Hydrochloric Acid 3 kg of 35% hydrochloric acid was added to 7.5 kg of a 25% sodium vinyl sulfonate aqueous solution (N-SVS-25: product of Asahi Kasei Finechem CO., LTD., Inc.). The mixture was stirred at room temperature for 30 minutes. Subsequently, sodium removal was performed by concentrating 4 L of an aqueous solution under reduced pressure, and filtering the deposited salt. This sodium removal process was performed two more times to exchange the sodium of the sodium vinyl sulfonate for hydrogen, thereby obtaining a vinyl sulfonic acid aqueous solution.

The sodium removal rate was 93.5% according to the acid value measured before sodium removal and the acid value measured after 3 applications of the sodium removal process.

The yield was 94.8% according to the iodine value measured before sodium removal and the iodine value measured after 3 applications of the sodium removal process.

COMPARATIVE EXAMPLE 2

Sodium Removal Process Using Hydrochloric Acid and Batch Distillation 4.5 kg of a vinyl sulfonic acid aqueous solution obtained in Comparative Example 1 was placed in a 5 L glass flask, and was subjected to distillation under reduced pressure so as to produce 2.1 kg of vinyl sulfonic acid. The recovery rate was 67%.

The decompression degree varied greatly, ranging from about 500 to 1000 Pa; that is, it was difficult to keep the decompression degree constant. Further, the obtained vinyl sulfonic acid was a deep, dark purple at the time of distillation. The residue was black and non-fluid.

COMPARATIVE EXAMPLE 3

Sodium Removal Process Using Hydrochloric Acid and Batch Distillation 1200 g of a vinyl sulfonic acid aqueous solution obtained in Comparative Example 1 was placed in a 1 L glass flask, and was subjected to distillation under reduced pressure so as to produce 740 g of vinyl sulfonic acid. The recovery rate was 82%. As with Comparative Example 2, the decompression degree varied greatly, ranging from about 500 to 1000 Pa; that is, it was difficult to keep the decompression degree constant. Further, the obtained vinyl sulfonic acid was deep, dark purple at the time of distillation. The residue was black and non-fluid.

COMPARATIVE EXAMPLE 4

Sodium Removal Process Using Hydrochloric Acid and Thin Film Distillation

The vinyl sulfonic acid aqueous solution obtained by Comparative Example 1 was subjected to distillation using a thin film evaporator (MS-300: product of SIBATA SCIENTIFIC TECHNOLOGY LTD.). However, distillation did not proceed due to the decomposed compounds adhering to the distillation surface.

EXAMPLE 1

Sodium Removal Process Using a Strongly Acidic a Ion Exchange Resin

Sodium removal was performed as follows. A column tower, 180 mm in internal diameter and 690 mm in height, was filled with 26 L of a strongly acidic ion exchange resin (Dowex Monosphere 650C) regenerated in advance using hydrochloric acid. 12.2 kg of 25% sodium vinyl sulfonate was applied into the column from the bottom. The column was then washed with 100 kg of ion exchange water, which was applied therein from the bottom. The sodium removal rate calculated from the acid value before and after sodium removal was 98.4%. The yield was 94.3%.

EXAMPLES 2-8

Sodium Removal Process Using a Strongly Acidic Ion Exchange Resin

For Examples 2 to 8, the same process as that of Example 1 was performed seven times. The ion exchange resin used in Example 1 was regenerated and recycled throughout Examples 2 to 8.

The regeneration of the exchange resin was conducted as follows. 5% hydrochloric acid was made to flow through the ion exchange resin column that was used in Example 1. The column was then washed with ion exchange water. This regeneration process was performed for each example so as to recycle the resin.

Table 1 shows the yields and sodium removal rates (rate of sodium exchange) for Examples 2 to 8.

TABLE 1

| | | |
|---|---|---|
| Example 2 | yield 96.5% | sodium removal rate 97.0% |
| Example 3 | yield 76.8% | sodium removal rate 99.8% |
| Example 4 | yield 84.6% | sodium removal rate 96.4% |
| Example 5 | yield 88.2% | sodium removal rate 96.9% |
| Example 6 | yield 82.3% | sodium removal rate 99.5% |
| Example 7 | yield 83.5% | sodium removal rate 97.8% |
| Example 8 | yield 70.6% | sodium removal rate 99.1% |

EXAMPLE 9

Sodium Removal Process Using a Strongly Acidic Ion Exchange Resin

Sodium removal was performed as follows. A column tower, 180 mm in internal diameter and 690 mm in height, was filled with 26 L of a strongly acidic ion exchange resin regenerated in advance with hydrochloric acid. 12.2 kg of 25% sodium vinyl sulfonate was applied into the column from the top. The column was then washed with 100 kg of ion exchange water, which was applied therein from the top. The sodium removal rate calculated from the acid value before and after the sodium removing process was 84.4%. The yield was 92.0%.

EXAMPLE 10

Sodium Removal Process Using a Strongly Acidic Ion Exchange Resin and Batch Distillation Under reduced pressure, 0.6 kg of the vinyl sulfonic acid composition obtained in the sodium removal process of Example 1 was concentrated. Then, a 500 mL-scale distillation was performed under reduced pressure. As a result, the decompression degree was kept at 150 Pa, and the recovery rate was 94%, though a slight smell of sulfurous acid gas was detected. The obtained vinyl sulfonic acid was light yellow at the time of distillation, and became more colored with time. The distillation produced a residue, but it was a dark brown fluid that was washed away easily.

EXAMPLE 11

Sodium Removal Process Using a Strongly Acidic Ion Exchange Resin and Batch Distillation A 1 L-scale distillation was performed in the same manner as that of Example 10, except that 1.2 kg of the vinyl sulfonic acid composition was used. As a result, a slight smell of sulfurous acid gas was detected. The decompression degree was about 220 Pa. The recovery rate was 92%. The obtained vinyl sulfonic acid was light yellow at the time of distillation, and became more deeply colored with time. The distillation produced a residue, but it was a dark brown fluid that was washed away easily.

EXAMPLE 12

Sodium Removal Process Using a Strongly Acidic Ion Exchange Resin and Batch Distillation A 2 L-scale distillation was performed in the same manner as that of Example 10, except that 2.4 kg of the vinyl sulfonic acid composition was used. As a result, a strong smell of sulfurous acid gas was detected. The decompression degree was about 360 Pa. The recovery rate was 89%. The obtained vinyl sulfonic acid was light yellow at the time of distillation, and became more deeply colored with time. The distillation produced a residue, but it was a dark brown fluid that was washed away easily.

EXAMPLE 13

Sodium Removal Process Using a Strongly Acidic Ion Exchange Resin and Batch Distillation A 5 L-scale distillation process was performed in the same manner as that of Example 10, except that 5 kg of the vinyl sulfonic acid composition was used. As a result, a significantly strong smell of sulfurous acid gas was detected. The decompression degree was about 600 Pa. The recovery rate was 78%. The obtained vinyl sulfonic acid was light yellow at the time of distillation, and became more deeply colored with time. The distillation produced a residue, but it was a dark brown fluid that was washed away easily.

EXAMPLE 14

Sodium Removal Process Using a Strongly Acidic Ion Exchange Resin and Thin Film Distillation Continuous distillations were performed with a thin film evaporator under reduced pressure by continuously feeding 3.6 kg of the vinyl sulfonic acid composition obtained in the sodium removal process of Example 1. The temperature range was 160-200° C. As a result, the decompression degree was kept at 70 Pa, and the continuous distillation operation was stably maintained. There was no smell of sulfurous acid gas at all. The recovery rate was about 96%.

The obtained vinyl sulfonic acid was light yellow at the time of distillation, and the color did not change even after six months. The distillation produced a residue, but it was a dark brown fluid that was washed away easily.

The invention claimed is:

1. A method for producing vinyl sulfonic acid, comprising: conducting demetallation of vinyl sulfonate salt, wherein the demetallation is carried out using strongly acidic ion exchange resin, and wherein a demetallation rate is not less than 95% according to the following formula:

$$\text{Demetallation rate}(\%) = \{(\text{acid value after demetallation})/(\text{acid value before demetallation})\} \times 100.$$

2. The method according to claim 1, wherein a product of the demetallation is purified by thin film distillation.

* * * * *